US008088265B2

(12) United States Patent
Rylatt et al.

(10) Patent No.: US 8,088,265 B2
(45) Date of Patent: Jan. 3, 2012

(54) CELL SEPARATION

(75) Inventors: Dennis Rylatt, Wheelers Hill (AU);
Sharon Leong, Earlwood (AU)

(73) Assignee: NuSep Holdings Ltd. (AU)

( * ) Notice: Subject to any disclaimer, the term of this patent is extended or adjusted under 35 U.S.C. 154(b) by 791 days.

(21) Appl. No.: 10/556,910

(22) PCT Filed: May 14, 2004

(86) PCT No.: PCT/AU2004/000636
§ 371 (c)(1),
(2), (4) Date: Jun. 20, 2007

(87) PCT Pub. No.: WO2004/101117
PCT Pub. Date: Nov. 25, 2004

(65) Prior Publication Data
US 2008/0067070 A1    Mar. 20, 2008

(30) Foreign Application Priority Data
May 15, 2003  (AU) ............................... 2003902363

(51) Int. Cl.
*B01D 57/02*    (2006.01)
(52) U.S. Cl. ............ 204/450; 204/543; 204/600; 435/2; 435/173.9
(58) Field of Classification Search ............... 204/450, 204/482, 516, 518, 520, 527, 540, 600, 627, 204/630, 543; 435/173.9, 2
See application file for complete search history.

(56) References Cited

U.S. PATENT DOCUMENTS

| 4,055,799 | A | * | 10/1977 | Coster et al. ................ 324/71.1 |
| 4,323,439 | A | * | 4/1982 | O'Farrell ..................... 204/468 |
| 5,071,536 | A | * | 12/1991 | Ivory ........................... 204/549 |
| 5,336,387 | A | * | 8/1994 | Egen et al. .................... 204/627 |
| 5,427,946 | A | | 6/1995 | Kricka et al. |
| 5,436,000 | A | | 7/1995 | Barbour et al. |
| 5,906,724 | A | * | 5/1999 | Sammons et al. ............ 204/627 |
| 6,001,617 | A | | 12/1999 | Raptis |
| 6,491,819 | B2 | * | 12/2002 | Prince et al. ............ 210/321.67 |
| 6,638,408 | B1 | | 10/2003 | Speicher et al. |
| 6,824,995 | B1 | * | 11/2004 | Wu ............................. 435/7.23 |
| 7,070,917 | B1 | | 7/2006 | Christensen et al. |
| 7,214,299 | B2 | * | 5/2007 | Armstrong ................... 204/455 |
| 7,399,394 | B2 | | 7/2008 | Weber |
| 2002/0043465 | A1 | * | 4/2002 | Vigh et al. ................... 204/548 |

(Continued)

FOREIGN PATENT DOCUMENTS
CN    1048168 A  *  1/1991
(Continued)

OTHER PUBLICATIONS
Translation of CN 1,048,168A, Jan. 1991.*
(Continued)

*Primary Examiner* — Kaj K Olsen
(74) *Attorney, Agent, or Firm* — McKeon, Meunier, Carlin & Curfman, LLC

(57) ABSTRACT

A process for separating a cell type from a mixture of cell types by electrophoresis comprising providing a sample containing a mixture of cell types to a sample chamber of membrane-based electrophoresis apparatus adapted to separate cells and applying an electric potential causing at least one cell type in the sample to be separated from other cells in the sample.

28 Claims, 1 Drawing Sheet

U.S. PATENT DOCUMENTS

| | | |
|---|---|---|
| 2002/0119218 A1 | 8/2002 | Burke, Jr. et al. |
| 2003/0029725 A1* | 2/2003 | Conlan et al. ............... 204/543 |
| 2009/0101507 A1 | 4/2009 | Aitken et al. |

FOREIGN PATENT DOCUMENTS

| | | |
|---|---|---|
| GB | 2360360 | 9/2001 |
| WO | WO0060065 | 10/2000 |
| WO | 0224314 | 3/2002 |
| WO | 02093168 | 11/2002 |
| WO | WO02093168 | 11/2002 |
| WO | 2004101117 | 11/2004 |

OTHER PUBLICATIONS

Barlow-Stewart, K. "Genes and Chromosomes" article produced by the Centre for Genetics Education downloaded from www.genetics.edu.au on Jun. 22, 2011. Last updated Jun. 10, 2011.

Engelmann et al. "Separation of Human X and Y Spermatozoa by Free-Flow Electrophoresis," Gamete Research 19:151-158 (1988).

Jaspers et al. "Separation of Bacterial Cells by Isoelectric Focusing, a New Method for Analysis of Complex Microboial Communities," Applied and Environmental Microbiology, Aug. 1997, pp. 3176-3181.

Klemm, M., "Device for extracting electrically charged molecules, useful e.g. in environmental monitoring or clinical diagnosis, comprises electrodes, container and matrix permeable to analyte," Derwent World Patents Index, Dialog File 351, Accession No. 15508313, 2 pages, Derwent Information Ltd. (2003).

McHenry, J. "International Search Report," PCT/AU2004/001367, 3 pages, Australian Patent Office, Australia (mailed Nov. 19, 2004).

Moore et al. "Isoelectric Focusing of Boar Spermatozoa," J. Reprod. Fert. (1975) 44, 329-332.

Moore "The Net Surface Charge of Mammalian Spermatozoa as Determined by Isoelectric Focusing, Changes Following Sperm Maturation, Ejaculation, Incubation in the Female Tract, and after Enzyme Treatment," International Journal of Andrology 2 (1979) 449-452.

Tilley, Breanna. "Assessment of Boar Sperm Samples by Computer-Assisted Sperm Analysis and the Mobility Assay," Master's Thesis. Texas Tech University, May 2007.

International Search Report. International Application No. PCT/AU2004/000636. Jun. 16, 2004.

* cited by examiner

CELL SEPARATION

RELATED APPLICATIONS

The present application is a U.S. National Phase Application of International Application PCT/AU2004/000636 (filed May 14, 2004) which claims the benefit of Australian Patent Application No. 2003902363 (filed May 15, 2003), all of which are herein incorporated by reference in their entirety.

TECHNICAL FIELD

The present invention relates to use of membrane-based electrophoresis technology for isolating/enriching a target cell population from a cell suspension preferably containing at least two types of cell populations.

BACKGROUND ART

Most cell separation methods provide enrichment of a cell population rather than true purification. Methods that provide pure cell preparations are often slow and have low recovery. A number of cell isolation/separation techniques have been employed previously for purifying/enriching or removing a cell population(s) from a suspension and can be divided into three categories (Kumar and Lykke, 1984, Pathology, (1):53-62). First, methods that exploit physical differences between cell populations (cell density, cell size, cell charge, optical properties) such as isopycnic density gradient centrifugation, velocity sedimentation, electrophoresis, phase partitioning, and flow cytometry. Secondly, methods in which separation is based upon differences in properties of the cell surface (adhesion, and surface antigen such as affinity and magnetic methods). Thirdly, methods that separate cells on the basis of their functional characteristics such as proliferation, phagocytosis, and antigen recognition.

Paradoxically, although the purpose is mainly to separate functionally different cell populations, there are very few existing methods that are actually based upon differences in cell function. Techniques based upon cell surface properties have good correlation with functional differences between cell populations. In recent years, those methods have been more widely used, especially in the area of stem cell purification. A disadvantage with using affinity methods, for example, is that they can often be expensive or time-consuming to perform and can cause considerable damage to, or activation of, desired cells and/or can add undesirable agents to the purified or isolated cell suspensions (e.g toxins, proliferation-inducing agents, and/or antibodies). An additional problem in the purification of stem cells using antibody-based methods is that the most primitive stem cells may not possess the antibody-targeted cell surface marker (e.g CD34) and such cells will not be recovered.

The most widely used techniques are those that rely on physical differences and electrophoresis falls into this category. The main form of electrophoresis used up to now is free-flow electrophoresis. This form involves laminar flow of cells through a specially designed chamber within an electric field. The different mobilities (different charge to mass ratios) of the cells in the electric field allows the cells to separate and they are collected through multiple channels at the end of the chamber. The extent to which these correlate with functional properties of the cells is variable.

Cell electrophoresis is a high resolution separation method. In traditional electrophoresis, sub-populations of cells for which no affinity ligand has been developed and for which there is no distinct size or density range are often separable on the basis of their electrophoretic mobility, which may be related to their function. The electrophoretic mobility of a cell is directly correlated with the cellular negative surface charge density.

The surface charge on cells will vary depending on the cell type, relative freshness of the cells, and the pH of the electrophoresis buffer used for separation. At physiological pH (around neutral), cells have a net negative surface charge and when placed in an electric field, they are deflected or moved towards the anode. In electrophoresis devices reported in the literature, fractionation is based on electrophoretic mobilities of the cells (Smolka, Margel et al, 1979, Biochim Biophys Acta, 588(2):246-55).

Some of the challenges faced by early investigators of electrophoretic cell separation were excessive heat generation, degree of resolution of the separated fractions and scalability of the technology.

The present inventors provide a reliable, reproducible, rapid, efficient, and cost-effective method of enriching a cell population of interest in its original state or selectively removing a cell subpopulation(s) from a cell suspension mixture based on physical differences between cell types using membrane-based electrophoresis technology.

DISCLOSURE OF INVENTION

The present invention relates to a process for separating a cell type from a mixture of cell types by electrophoresis comprising providing a sample containing a mixture of cell types to a sample chamber of membrane-based electrophoresis apparatus adapted to separate cells and applying an electric potential causing at least one cell type in the sample to be separated from other cells in the sample.

In a first aspect, the present invention provides a process for separating a cell type from a mixture of cell types by electrophoresis, the process comprising:
(a) providing a sample containing a mixture of cell types to a sample chamber of electrophoresis apparatus comprising a first electrolyte chamber; a second electrolyte chamber, a first sample chamber disposed between the first electrolyte chamber and the second electrolyte chamber; a second sample chamber disposed adjacent to the first sample chamber disposed and between the first electrolyte chamber and the second electrolyte chamber; a first ion-permeable barrier disposed between the first sample chamber and the second sample chamber; a second ion-permeable barrier disposed between the first electrolyte chamber and the first sample chamber, a third ion-permeable barrier disposed between the second sample chamber and the second electrolyte chamber; and electrodes disposed in the first and second electrolyte chambers; and
(b) applying an electric potential between the electrodes causing at least one cell type in the first sample chamber or the or second sample chamber to move through the first ion-permeable barrier into the other of the first or second sample chamber.

The cell can be any cell type including cancer, totipotent, multipotent, pluripotent, stem, viable, non-viable, bacterial, erythrocyte, leukocyte, bone marrow, organ, tissue, single cell eukaryote, prokaryote, algae, plant, or disease causing and/or diagnostically important cell. Preferably, at least one cell type is selected from erythrocyte, leukocyte, bone marrow cell, organ cell, stem cell, and tissue cell.

In one preferred embodiment, the sample contains at least two cell populations. The cell types can be derived from the same cell species but having different characteristics such as cell surface modifications for example, or can be of different cell types.

The cell type of interest is caused to move out of the sample through the first ion-permeable barrier into the other of the first or second sample chamber and unwanted cell types remain in the sample during electrophoresis. Alternatively, the cell type of interest may remain in the sample and unwanted cell types are caused to move out of the sample into the other of the first or second sample chamber during electrophoresis.

Preferably, substantially all trans-barrier migration of the desired cell type(s) occurs upon the application of the electric potential.

In another preferred embodiment the step of applying an electric potential between the electrodes is maintained until at least one cell type reaches a desired purity level in the first or second sample chamber.

In one embodiment, the first ion-permeable barrier is an electrophoresis membrane having a characteristic average pore size and pore size distribution. In another embodiment, all the ion-permeable barriers are membranes having a characteristic average pore size and pore size distribution. This configuration of the apparatus is suitable for separating cells on the basis of charge and or size.

At least some of the electrophoresis separation membranes are preferably made from polyacrylamide and have a molecular mass cut-off of at least about 5 kDa. The molecular mass cut-off of the membrane will depend on the sample being processed, the other molecules in the sample mixture, and the type of separation carried out. Preferably, the first barrier is a large pore sized membrane such as a polycarbonate membrane, polyacrylamide membrane, polyvinyl alcohol (PVA), polyethersulfone (PES), polyvinylidene fluoride (PVDF), nylon, acrylic copolymer based, vinyl coplymer based, polysulfone, cellulose, cellulose triacetate, cellulose esters, polypropylene, silicates, borosilicates and/or glass fiber.

The large pore size is preferably sufficiently large enough to allow the passage of a desired cell type under electromotive force in the apparatus. Preferably, the large pore size is from about 0.01 to 100 μm. More preferably, the pore size is from about 1 to 10 μm. It will be appreciated, however, that the pore size can be selected based on the size of the cells to be separated.

The second and third barriers are preferably restriction membranes having a molecular mass cut off less than that of the first membrane. A restriction membrane is also preferably formed from polyacrylamide. The molecular mass cut-off of the restriction membranes will depend on the sample being processed, the other molecules in the sample mixture, and the type of separation carried out. It will be appreciated that the second ion-permeable barrier may have a different molecular mass cut off to the third ion-permeable barrier.

The first ion-permeable barrier preferably prevents substantial convective mixing of contents of the first and second sample chambers, the second ion-permeable barrier preferably prevents substantial convective mixing of contents of the first electrolyte chamber and the first sample chamber, and the third ion-permeable barrier preferably prevents substantial convective mixing of contents of the second electrolyte chamber and the second sample chamber.

In another embodiment, the second and third ion-permeable barriers are membranes having characteristic average pore size and pore-size distribution.

At least about 50% of the at least one cell type preferably remains viable or substantially unchanged after separation.

Preferably, at least about 60%, more preferably at least about 70%, even more preferably at least about 80%, or up to about 90% of the at least one cell type remains viable or substantially unchanged after separation.

The present invention can result in recovery rates of at least 50% active cell type of choice. Preferably, the recovery rates are much higher and in the order of 70% or greater.

The sample may be processed in a static form in batches or may be processed by moving the sample and electrolyte in streams through the apparatus. By convenience, the first sample chamber is called stream 1 and the second sample chamber is called stream 2.

Preferred voltages of range from about 1 to 200 V. Experiments with cells have found that 60 V is suitable with the apparatus used.

Field strengths of about 10 to 100V/cm are preferred. Experiments with cells have found that 50 V/cm is suitable with the apparatus used.

Electrophoresis run times ranging from about 2 to 60 mins are suitable. Experiments with cells have found that 10 minutes is suitable with the apparatus used.

It will be appreciated that voltage, field strength and electrophoresis run times can vary depending on the cell type, apparatus and medium used. It is within the skill of the operator to determine optimum conditions for a given cell separation run.

Preferred buffer or electrolyte concentrations are between about 100 to 400 mM. Any suitable buffer or electrolyte can be used. Suitable buffers or electrolytes include, but not limited to, cell-compatible biological buffers and components such as HEPPS, HEPES, BisTris, sodium chloride, phosphate buffer salts, sucrose, glucose and mannitol. In experiments outlined below, a 270 mM buffer of HEPPS, BisTris, NaCl, sucrose and glucose has been found to be suitable. It will be appreciated, however, that any other suitable buffer can be used.

Cell concentrations of between about $10^5$ to $10^{10}$ can be processed by the present invention. Concentrations of between $10^6$ to $10^8$ sells have been successfully separated by the present inventors.

In a second aspect, the present invention provides an isolated cell type obtained by the process according to the first aspect of the present invention.

In a third aspect, the present invention provides use of a membrane-based electrophoresis apparatus to separate a cell type from a mixture of cell types, wherein at least about 50% of the at least one cell type remains viable or substantially unchanged after separation.

Gradiflow™ and Microflow™ are trade marks owned by Gradipore Limited, Australia.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred embodiments will be described with reference to the following drawings and examples.

MODE(S) FOR CARRYING OUT THE INVENTION

Figure 1:
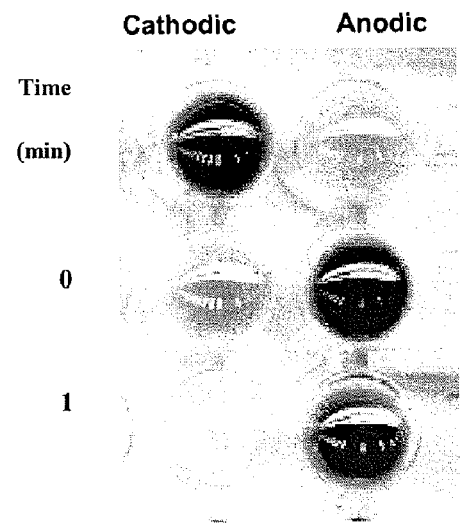
FIG. 1 shows a time course of erythrocyte movement in the electrophoresis apparatus.

Before describing the preferred embodiments in detail, the principal of operation of a membrane-based electrophoresis apparatus will first be described. An electric field or potential applied to ions in solution will cause the ions to move toward one of the electrodes. If the ion has a positive charge, it will move toward the negative electrode (cathode). Conversely, a negatively-charged ion will move toward the positive electrode (anode).

In the apparatus used for present invention, ion-permeable barriers that substantially prevent convective mixing between the adjacent chambers of the apparatus or unit are placed in an electric field and a cell type or population in the sample is selectively transported through an ion-permeable barrier. The particular ion-permeable barriers used will vary for different applications and generally have characteristic average pore sizes and pore size distributions and/or isoelectric points allowing or substantially preventing passage of different components.

Apparatus

A number of membrane-based electrophoresis apparatus have been developed by, or in association with, Gradipore Limited, Australia. The apparatus are marketed and used under the Gradiflow™ name. In summary, the apparatus typically includes a cartridge which houses a number of membranes forming at least two chambers, cathode and anode in respective electrode chambers connected to a suitable power supply, reservoirs for samples, buffers and electrolytes, pumps for passing samples, buffers and electrolytes, and cooling means to maintain samples, buffers and electrolytes at a required temperature during electrophoresis. The cartridge contains at least three substantially planar membranes disposed and spaced relative to each other to form two chambers through which sample or solvent can be passed. A separation membrane is disposed between two outer membranes (termed restriction membranes as their molecular mass cut-offs are usually smaller than the cut-off of the separation membrane). When the cartridge was installed in the apparatus, the restriction membranes are located adjacent to an electrode. The cartridge is described in AU 738361. Description of membrane-based electrophoresis can be found in U.S. Pat. No. 5,039,386 and U.S. Pat. No. 5,650,055 in the name of Gradipore Limited, incorporated herein by reference. An apparatus particularly suitable for use in isoelectric separation applications can be found in WO 02/24314 in the name of The Texas A&M University System and Gradipore Limited, incorporated herein by reference. An other apparatus suitable for the present invention, originally developed to separate macromolecules in small volumes, is described in WO 01/78878, incorporated herein by reference.

One electrophoresis apparatus suitable for use in the present invention comprises:

(a) a first electrolyte chamber;
(b) a second electrolyte chamber,
(c) a first sample chamber disposed between the first electrolyte chamber and the second electrolyte chamber;
(d) a second sample chamber disposed adjacent to the first sample chamber disposed and between the first electrolyte chamber and the second electrolyte chamber;
(e) a first ion-permeable barrier disposed between the first sample chamber and the second sample chamber, the first ion-permeable barrier prevents substantial convective mixing of contents of the first and second sample chambers;
(f) a second ion-permeable barrier disposed between the first electrolyte chamber and the first sample chamber, the second ion-permeable barrier prevents substantial convective mixing of contents of the first electrolyte chamber and the first sample chamber;
(g) a third ion-permeable barrier disposed between the second sample chamber and the second electrolyte chamber, the third ion-permeable barrier prevents substantial convective mixing of contents of the second electrolyte chamber and the second sample chamber; and
(h) electrodes disposed in the first and second electrolyte chambers.

The electrophoresis apparatus may further comprise one or more of:

(i) an electrolyte reservoir;
j) a first sample reservoir and a second sample reservoir;
(k) means for supplying electrolyte from the electrolyte reservoir to the first and second electrolyte chambers; and
(l) means for supplying sample or liquid from at least the first sample reservoir to the first sample chamber, or from the second sample reservoir to the second sample chamber.

The apparatus may further comprise:

(m) a first electrolyte reservoir and a second electrolyte reservoir; and
(n) means for supplying electrolyte from the first electrolyte reservoir to the first electrolyte chamber and electrolyte from second electrolyte reservoir to the second electrolyte chamber.

The apparatus may further comprise one or more of:

means for circulating electrolyte from the electrolyte reservoir(s) through the electrolyte chambers forming electrolyte streams in the electrolyte chambers; and means for circulating contents from each of the first and second sample reservoirs through the respective first and second sample chambers forming first and second sample streams in the respective sample chambers;

means for removing and replacing sample in the first or second sample reservoirs; and means to maintain temperature of electrolyte and sample solutions.

In one form, the first ion-permeable barrier is a membrane having a characteristic average pore size and pore size distribution. In one preferred form, all the ion-permeable barriers are membranes having a characteristic average pore size and pore size distribution. This configuration of the apparatus is suitable for separating compounds on the basis of charge and or size.

In another form, the second and third ion-permeable barriers are membranes having a characteristic average pore size and pore-size distribution.

In order to control substantial bulk movement of liquid under the influence of an electric field an inducible electro-endo-osmotic membrane can be used in at least one of the second or third ion-permeable barriers. The inducible electro-endo-osmotic membrane is preferably a cellulose tri-acetate (CTA) membrane. It will be appreciated that the inducible electro-endo-osmotic membrane can be formed from any other suitable membrane material such as poly(vinyl alcohol) cross-linked with glutaraldehyde (PVAl+glut).

The present inventors have found that a CTA membrane having a nominal molecular mass cut-off of 5, 10 or 20 kDa are particularly suitable for use in the apparatus. It will be appreciated that other molecular mass cut-offs would also be suitable for the apparatus.

The present inventors have found that a polycarbonate membrane having a molecular mass cut off of about 5 μm is also suitable for use in the apparatus. It will be appreciated that other molecular mass cut-offs would also be suitable for the apparatus.

The electrophoresis apparatus may contain a separation unit housing the chambers and ion-permeable barriers which is provided as a cartridge or cassette fluidly connected to the electrolyte reservoir(s) and, if present, the sample reservoirs.

In use, a sample containing cells to be separated is placed in the first or second sample chamber. Electrolyte is placed in the first and second electrolyte chambers. Electrolyte or other liquid can be placed in the first and/or second sample chamber. An electric potential is applied to the electrodes wherein a cell type in the first and/or second sample chamber is caused to move through a diffusion barrier to the second and/or first sample chamber.

Results

An example of an application for the present invention has been in the area of blood cell fractionation. A method has been developed for separating leukocyte and erythrocyte-containing blood or blood fraction (for example, buffy coat) into a fraction enriched for leukocytes (≧80% of the original leukocytes are recovered) and another fraction enriched for erythrocytes using a bench top analytical-scale apparatus, termed the Microflow™ apparatus by Gradipore Limited. This apparatus was originally developed to separate macromolecules in small volumes and is described in WO 01/78878, incorporated herein by reference.

Because erythrocytes (~7 μm diameter) and leukocytes (8-20 μm diameter) differ in size, a separation strategy based on a combination of size and charge was employed.

Erythrocytes

To initially determine the experimental conditions used to move cells in the electrophoresis apparatus whilst preserving their viability, erythrocytes were used as a model system. Only cell preparations with high viability (i.e >90%) were considered for separation. Details of the experiment is outlined below:
Buffer: Bis Tris, HEPES, NaCl, glucose, sucrose, pH 7.4
Conductivity: 4 mS/cm
Separation Membrane: 10 μm polycarbonate
Restriction Membrane: 5 kDa polyacrylamide
Cathodic chamber: 420 μl RBC ($10^8$ cells/mL)
Anodic chamber: 420 μl buffer
Electric field strength: 50 V/cm The colour of erythrocytes provided a qualitative indication of their movement in the electrophoresis apparatus. The cathodic and anodic chambers were sampled at the times indicated in FIG. 1. At zero time, when no voltage was applied, erythrocytes were mainly restricted to the cathodic chamber. The slight reddish colour in the anodic chamber may represent cell-free hemoglobin released from fragmented cells. One minute after applying voltage, a major proportion of erythrocytes had transferred to the anodic chamber, and after 2 min, the transfer was almost complete. Viability of the cells was preserved as assessed by trypan blue exclusion test. Electroendo-osmosis was apparent by the bulk movement of fluid in the apparatus.

Leukocytes

Once conditions for erythrocyte movement in electrophoresis apparatus was established, these conditions formed a basis for separating erythrocytes from leukocytes in buffy-coat enriched blood obtained from the Australian Red Cross. Leukocytes constitute <1% of total cells in blood, however, this number is slightly increased in buffy-coat coat enriched blood. Leukocytes in the sample cell preparation were enriched prior to separation in the electrophoresis apparatus to allow for easy analysis following separation.

Leukocytes were obtained by allowing the blood cells to sediment into their layers under unit gravity at room temperature for 2 to 4 h. The cell suspension for separation was prepared by mixing erythrocytes:leukocytes at a 1:1 ratio and diluting the mixture with separation buffer to achieve a cell concentration of about $10 \times 10^6$ cells/ml. In addition, the initial cell preparation was diluted with buffer to lower the conductivity of the plasma from 12 mS/cm to 4 mS/cm for effective cell separation to occur. Conditions used to remove erythrocytes from the cell mixture, thereby enriching for the leukocytes were similar to those used for the movement of erythrocytes described above except for:
Separation Membrane: 5 μm polycarbonate
Cathodic chamber: 420 μl RBC+WBC ($10^6$ cells/ml)

Figure 2:
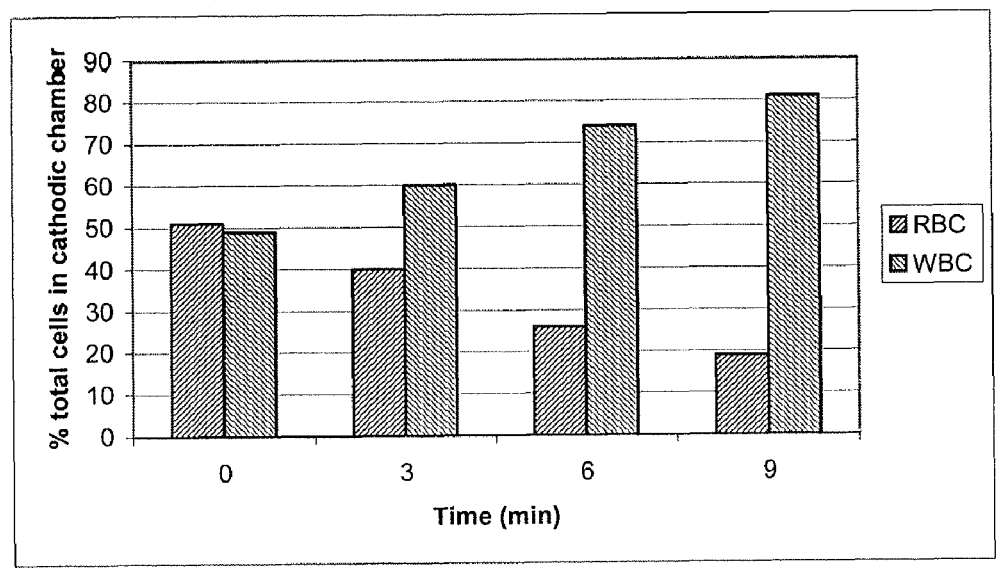
FIG. 2 is a graph of the time course of erythrocyte removal from an erythrocytes/leukocytes suspension mixture.

The results of the time course of erythrocyte removal from the erythrocytes/leukocytes suspension mixture are shown in FIG. 2. Before applying voltage, approximately equal proportions of erythrocytes:leukocytes was present in the cell suspension. Between 3 & 9 min of electrophoresis, the proportion of erythrocytes in the cathodic chamber decreased as most erythrocytes transferred across the separation membrane which represents a barrier to the larger leukocytes. The leukocyte population in the cathodic chamber was highly-enriched (~80%) after 9 min electrophoresis (FIG. 2). The viability of the cells was maintained after 9 min run. Electroendo-osmosis was observed and increased with higher cell concentrations.

SUMMARY

The present invention uses a membrane-based electrophoresis system, called Gradiflow™, designed to enrich for, or remove, a cell population(s) from a cell suspension mixture of cell types. Central to the technology is a disposable membrane cartridge consisting of at least two membranes housed within the separation unit of the instrument. An arrangement of ≧1 separation membrane(s) between 2 restriction membranes forms (n+1) chambers, where n is the number of separation membranes inserted. Electrophoresis buffer is positioned or circulates on the outside of the restriction membranes and performs the dual function of setting the pH of the system and cooling the electrophoresis chamber. Application of an electric potential induces migration of the cells within the separation unit. By selecting an appropriate separation membrane pore size, isolation of cells by size fractionation can be achieved.

The present invention details the first membrane-based electrophoretic system applied to the separation/removal of a cell population from a cell suspension containing at least two different cell types. Unlike traditional electrophoresis devices in which separation is based on relative electrophoretic mobilities of different cell types, the present membrane-based electrophoresis technology separates cells based on the combination of size and electrophoretic mobility. Advantages associated with the present invention for cell separation are that it is rapid and gentle, and preserves the in vivo status of the cells. This is in contrast to antibody-based methods which require an enzyme or chemical process to remove the affinity ligand bound to the cell surface, and thus may alter the cell surface properties.

Cell separation has an important application in blood transfusion. Transfusion of whole blood containing donor leukocytes to a recipient can be harmful because certain cell types can cause irreversible damage to the blood recipients organs in immunocompromised patients.

Other applications where the present invention has particular utility involve the purging of cancer cells from cell suspensions and the isolation and enrichment of stem cells from cell suspensions. These applications are important components in many clinical treatment therapies involving, for example, cancer treatment, organ transplant, and gene therapy. Patients receiving cancer therapies (intensive chemotherapy/irradiation) require stem cell transplants in order to survive the effects of the therapy. Stem cell-containing tissue for transplant may be derived from donor bone marrow (allogeneic transplant) or from the patient's own bone marrow or peripheral blood after mobilisation (autologous transplant). In both instances, there is a need for effective cell separation methods to enrich the transplant tissue in stem cells and reduce the number of undesirable and deleterious cells (e.g mature T cells in allogeneic transplants and residual cancer cells in autologous transplants).

A variety of gene therapies involving genetically manipulated stem cells are under development for treating a variety of blood-related diseases (e.g AIDS, leukemia, other cancers).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for separating a cell type from a mixture of cell types by electrophoresis comprising:
   (a) providing a sample comprising between about $10^5$ to about $10^{10}$ cells/mL of a mixture of cell types to a first or second sample chamber of an electrophoresis apparatus, wherein said electrophoresis apparatus comprises a first electrolyte chamber; a second electrolyte chamber, a first sample chamber disposed between the first electrolyte chamber and the second electrolyte chamber; a second sample chamber disposed adjacent to the first sample chamber disposed and between the first electrolyte chamber and the second electrolyte chamber; a first ion-permeable membrane disposed between the first sample chamber and the second sample chamber; a second ion-permeable membrane disposed between the first electrolyte chamber and the first sample chamber; a third ion-permeable membrane disposed between the second sample chamber and the second electrolyte chamber; and the electrodes disposed in the first and second electrolyte chambers; and
   (b) applying an electric potential between the electrodes causing at least one cell type in the first sample chamber or the second sample chamber to move through the first ion-permeable membrane into the other of the first or second sample chamber
   wherein substantially all transmembrane migration of a desired cell type occurs upon the application of the electric potential.

2. The process according to claim 1 wherein the at least one cell type is selected from the group consisting of erythrocyte and leukocyte bone marrow.

3. The process according to claim 1 wherein the sample comprises at least two cell populations.

4. The process according to claim 1 wherein a cell type of interest moves out of the sample through the first ion-permeable membrane into the other of the first or second sample chamber and unwanted cell types remain in the sample during electrophoresis, or the cell type of interest remains in the sample and unwanted cell types are caused to move out of the sample into the other of the first or second sample chamber during electrophoresis.

5. The process according to claim 1 wherein the first ion-permeable membrane prevents substantial convective mixing of contents of the first and second sample chambers, the second ion-permeable membrane prevents substantial convective mixing of contents of the first electrolyte chamber and the first sample chamber, and the third ion-permeable membrane prevents substantial convective mixing of contents of the second electrolyte chamber and the second sample chamber.

6. The process according to claim 1 wherein the step of applying an electric potential between the electrodes is maintained until at least one cell type reaches a desired purity level in the first or second sample chamber.

7. The process according to claim 1 wherein the first ion-permeable is membrane has a characteristic average pore size and pore size distribution.

8. The process according to claim 1 wherein all the ion-permeable membranes have a characteristic average pore size and pore size distribution.

9. The process according to claim 8 wherein at least a portion of the membranes are made from polyacrylamide and have a molecular mass cut-off of at least about 5 kDa.

10. The process according to claim 8 wherein the first membrane is a large pore sized membrane selected from the group consisting of a polycarbonate membrane, a polyacrylamide membrane, a polyvinyl alcohol (PV A) membrane, a polyethersulfone (PES) membrane, a polyvinylidene fluoride (PVDF) membrane, a nylon membrane, an acrylic copolymer based membrane, a vinyl copolymer based membrane, a polysulfone membrane, a cellulose membrane, a cellulose triacetate membrane, a cellulose ester, a polypropylene membrane, a silicate, a borosilicate, and a glass fiber.

11. The process according to claim 10 wherein the large pore sized membrane is a polycarbonate membrane.

12. The process according to claim 10 or 11 wherein the pore size is from about 0.01 to about 100 μm.

13. The process according to claim 12 wherein the pore size is from about 1 to about 10 μm.

14. The process according to claim 1 wherein the second and third membranes are restriction membranes having a molecular mass cut off less than that of the first barrier.

15. The process according to claim 14 wherein the restriction membranes are formed from polyacrylamide.

16. The process according to claim 1 wherein at least about 50% of the at least one cell type remains viable or substantially unchanged after separation.

17. The process according to claim 16 wherein at least about 60% of the at least one cell type remains viable or substantially unchanged after separation.

18. The process according to claim 1 wherein the sample is processed in a static form in batches or processed in a substantially continuous form by moving the sample and electrolyte in streams through the apparatus.

19. The process according to claim 18 wherein the field strength is about 50 V/cm.

20. The process according to claim 1 wherein the difference in the electric potential is from about 1 to about 200 V.

21. The process according to claim 20 wherein the voltage is about 60 V.

22. The process according to claim 20 wherein the field strengths are from about 10 to about 100 V/cm.

23. The process according to claim 1 wherein the electric potential is applied for a period of from about 1 to about 60 minutes.

24. The process according to claim 23 wherein the electrophoresis run time is about 10 minutes.

25. The process according to claim 1 wherein buffer or electrolyte concentrations are between about 100 to about 400 mM.

26. The process according to claim 25 wherein the buffer or electrolyte is a cell-compatible biological buffer comprising at least one component selected from the group consisting of HEPPS, HEPES, BisTris, sodium chloride, phosphate buffer salts, sucrose, glucose and mannitol.

27. The process according to claim 1 wherein the cell concentration of the sample is between about $10^6$ and about $10^8$ cells/mL.

28. The process according to claim 1, wherein movement of the desired cell type though the membrane due to the electric potential is substantially greater than any convective movement of the desired cell type though the membrane.

* * * * *